US005665687A

United States Patent [19]
Khayat et al.

[11] Patent Number: 5,665,687
[45] Date of Patent: Sep. 9, 1997

[54] CLEANING COMPOSITION CONTAINING LIPID GRAINS

[75] Inventors: Carine Khayat, la Varenne; Didier Candau, Bievres, both of France

[73] Assignee: L'Oreal, Paris, France

[21] Appl. No.: 491,697

[22] Filed: Jun. 19, 1995

[30] Foreign Application Priority Data

Jun. 17, 1994 [FR] France .................. 94 07481

[51] Int. Cl.$^6$ .................. C11D 3/302; C11D 3/46; A61K 47/44
[52] U.S. Cl. .................. 510/136; 510/139; 510/159; 510/417
[58] Field of Search .................. 252/174.22, 168, 252/DIG. 1, DIG. 5, 174.25, 174, 90, 91, 169; 424/401; 514/846; 510/136, 139, 159, 417

[56] References Cited

U.S. PATENT DOCUMENTS

| | | | |
|---|---|---|---|
| 4,014,995 | 3/1977 | Juliano et al. | 424/168 |
| 4,781,916 | 11/1988 | Papaphilippou | 424/61 |
| 4,788,345 | 11/1988 | Sebag et al. | 568/623 |
| 4,883,659 | 11/1989 | Goodman et al. | 424/78 |
| 4,946,670 | 8/1990 | Sebag et al. | 424/47 |
| 5,011,681 | 4/1991 | Ciotti et al. | 424/81 |
| 5,039,516 | 8/1991 | Goodman et al. | 424/59 |
| 5,198,210 | 3/1993 | Critchley et al. | 424/78.03 |
| 5,206,020 | 4/1993 | Critchley et al. | 424/401 |
| 5,326,565 | 7/1994 | Critchley et al. | 424/401 |
| 5,415,885 | 5/1995 | Critchley et al. | 424/61 |
| 5,439,935 | 8/1995 | Rawlings et al. | 514/451 |
| 5,443,760 | 8/1995 | Kasprzak | 424/78.03 |
| 5,532,000 | 7/1996 | Kauffmann | 424/450 |

FOREIGN PATENT DOCUMENTS

| | | |
|---|---|---|
| 376852 | 7/1990 | European Pat. Off. . |
| 2649608 | 1/1991 | European Pat. Off. . |
| 412865 | 2/1991 | European Pat. Off. . |
| 452202 | 10/1991 | European Pat. Off. . |
| 0 506 197 | 9/1992 | European Pat. Off. . |
| 2 649 608 | 1/1991 | France . |

*Primary Examiner*—Paul Leiberman
*Assistant Examiner*—Gregory R. Delcotto
*Attorney, Agent, or Firm*—Oblon, Spivak, McClelland, Maier & Neustadt, P.C.

[57] ABSTRACT

A skin-cleansing composition in the form of an oil-in-water emulsion. This emulsion comprises an emulsifying agent of hydrophilic/lipophilic balance below about 12 and lipid grains containing a cleansing agent. The invention composition constitutes a "3 in 1" product, which simultaneously allows cleansing, scrubbing and care of the skin.

13 Claims, No Drawings

CLEANING COMPOSITION CONTAINING LIPID GRAINS

BACKGROUND OF THE INVENTION

1. Field of the Invention

The present invention relates to a skin-cleansing composition in the form of an oil-in-water (O/W) emulsion, which may be used for cleansing the skin of the human face, neck and/or body. In particular, this composition, which enables dead cells to be removed gently from the skin, constitutes a "3 in 1" product which is particularly suitable for sensitive skins.

The invention also relates to a process for cleansing the skin of the body and/or face.

2. Discussion of the Background

Exfoliant or scrubbing products, also referred to as "scrubs", contain exfoliant particles which consist of abrasive materials such as polyethylene powder, walnut shell powder or apricot or almond powder. Unfortunately, these scrubbing products are irritating due to the very presence of these particles which rub the skin without melting and which remain on its surface. On account of their irritant nature, it is not possible to use these scrubbing products daily; depending on the sensitivity, there must be longer or shorter time intervals between uses thereof, in particular of several days, or even of several weeks for very sensitive skin. Moreover, in order to overcome skin irritation, it is necessary, after use, to apply a care cream which provides protection and moisturization to the skin.

There thus is a need for a scrubbing-product which is comfortable to use, which does not contain abrasive exfoliant particles and which does not require the subsequent application of a care cream.

The composition according to the present invention overcomes the drawbacks described above. Applicant has found, surprisingly, that it is possible to have a "3 in 1" scrubbing product, that is to say a product which simultaneously cleanses, scrubs and cares for the skin, containing no abrasive particles, by providing an oil-in-water emulsion comprising lipid grains filled with a cleansing agent.

SUMMARY OF THE INVENTION

One embodiment of the present invention is a skin-cleansing composition in the form of an oil-in-water emulsion comprising an emulsifying agent having a hydrophilic-lipophilic balance below or equal to about 12.5 and solid, non-hydrophilic lipid grains having a melting point below 50° C., these grains incorporating a cleansing agent.

Another embodiment of the present invention is a make-up removing composition comprising the composition defined above where the cleansing agent has make-up removing action.

Another embodiment of the present invention is a process for cleansing and/or scrubbing the skin of the body and/or face and/or neck, including the arms, legs, torso, front and back of each, head, scalp, eyelids, etc., comprising applying to skin the composition defined above, and/or massaging the skin with the composition in order to remove the dead cells, and optionally rinsing the skin.

A further embodiment of the present invention is the use of the composition defined above for cleansing and/or scrubbing the skin of the human body and/or face and/or neck, etc.

FR-A-2,649,608 described the use, in an aqueous gel, of grains consisting of a solid, non-hydrophilic lipid substance having a melting point below 50° C., in order to make the gel more comfortable to apply. However, this gel, even when charged with lipid grains, is less comfortable to use than an emulsion and cannot provide the level of skin care effect that an emulsion does on account of the absence of oil therein. It is not obvious to incorporate these lipid grains into an emulsion. Indeed, under certain conditions, the incorporation of lipid grains into an oil-in-water emulsion causes fusion of the lipid substance or substances of the grains with the oily phase, to the extent that the product obtained can no longer serve to scrub and/or cleanse the skin. This fusion also occurs in a water-in-oil emulsion: the lipid substance or substances of the grains fuse with the continuous phase and the emulsion obtained is unstable.

Applicant has discovered, however, that by using an oil-in-water emulsion and an emulsifying agent having a hydrophilic-lipophilic balance (HLB) below about 12.5, and more particularly between about 6 and about 12, it is possible to incorporate the lipid grains into an emulsion without the grains fusing with the oily phase. However, if emulsifying agents having a hydrophilic-lipophilic balance above 12.5 are used, as is commonly the case for the preparation of oil-in-water emulsions, it is observed that the lipid substance or substances of the grains have a tendency to dissolve in the oily phase of the emulsion, an shown by the comparative examples given below.

The composition according to the present invention has a triple action. That is, it has, in effect, a cleansing action, a scrubbing action and a caring action.

Cleansing of the skin is obtained by virtue of the presence of lipid grains which contain a cleansing agent that absorbs skin dirt and impurities. Moreover, in the case of the removal of make-up, the grains, which are lipophilic, melt into the make-up to give better subsequent removal thereof.

Scrubbing of the skin in achieved by massaging the invention composition containing grains on the skin, which causes the removal of dead cells; the grains melt during this mechanical action, without giving rise to irritation. The skin care effect is obtained with the present invention by virtue of the texture and the choice of constituents of the emulsion: oils and active agents.

DETAILED DESCRIPTION OF THE PREFERRED EMBODIMENTS

As indicated above, the emulsifying agent which is used in the invention should have a hydrophilic-lipophilic balance below about 12, and more particularly between about 6 and 12. It is possible to use any emulsifying agent having the proper HLB, including cetearyl glucoside sold under the name Montanov 68 by Seppic, which has an HLB value of 10. It is also possible to use mixtures of emulsifying agents which give a final HLB value below about 12.5, preferably ranging from about 6 to 12, the emulsifying agents being chosen, for example, from agents including sorbitan stearate or tristearate, PEG-40 stearate, PEG-50 stearate, PEG-100 stearate, glyceryl stearate and polysorbate 60.

In the composition according to the invention, it is preferred for the melting point of the lipid grains to be below 50° C., and more preferably to melt in the range of from 30° to 45° C., such that the grains melt simply by applying to the body, with gentle rubbing or massaging in.

Among the solid, non-hydrophilic lipid substances forming lipid grains which may be used in the invention, there may in particular be mentioned semi-synthetic glycerides, certain natural fatty substances and certain synthetic fatty compounds.

Preferred semi-synthetic glycerides include linear saturated fatty acid triglycerides having from 8 to 18 carbon atoms, with a hydroxyl number <30 and an iodine number <3, and among these, those sold under the names Lipocire or Suppocire by Gattefosse, and in particular Lipocire A or DM, Suppocire AIM, AM, BM, CM, DM, AI, A, B, C and D, and those sold under the names Witepsol or Softisan by Dynamit Nobel, and in particular Witepsol $H_{32}$, $H_{35}$, $H_{37}$, $H_{39}$ and $H_{42}$ may be used.

Natural fatty substances include butters or solid fractions of plant fats such as, for example, karite butter, cocoa butter, coconut oil and derivatives thereof. Synthetic fatty compounds include silicone waxes such as the products sold by Wacker under the name Cire silicone VP 1622 or Silicone Copolymer F 755.

The lipid substances mentioned above may be used alone or in the form of a mixture, and, in the latter case, it is preferable to speak of a melting region or a melting zone, rather than a melting point which is preferably within the above ranges.

It is also possible according to the invention to use lipid substances having a melting point or melting zone above 50° C., but, in this case, it is necessary to make use of the presence of a lipid adjuvant having a lower melting point or zone in order to adjust the melting point or melting zone of the lipid mixture to a value below 50° C.

Lipid substances with a melting point above 50° C. include triglycerides such as Softisan 154 sold by the company Dynamit Nobel, animal, plant, mineral or synthetic waxes or derivatives thereof, and in particular beeswax, spermaceti, candelilla wax and hydrogenated derivatives thereof, carnauba wax and hydrogenated derivatives thereof, paraffins, ozokerites and the product marketed under the name Elfacos $C_{26}$ by Akzo Chemie.

Lipid adjuvants intended to lower the melting point of the lipid substances melting above 50° C. include linear $C_{14}$ and $C_{16}$ saturated fatty alcohols, branched $C_{12}$ to $C_{24}$ alcohols, fatty esters, unsaturated fatty acids, complex mixtures of lipids such as plant oils, and silicone oils.

In addition, it is possible, in order to adjust the consistency or the viscosity of an lipid grains, to introduce into the mixture modified clays or an oily dispersion thereof, silicas, metal soaps or any other structuring agent for fatty substances. In order to adjust the hardness of the grains, it is possible to introduce, for example, glyceryl monodiisostearate.

The cleansing agent contained in the grains of the composition of the invention may be chosen from, for example, cereal flours, clays and make-up removing oils. Mixtures may be used. According to a preferred embodiment of the invention, the cleansing agent is a cereal flour.

While it is known to use flours to cleanse the skin (see, in this regard, FR-A-2,499,097), their introduction into a cosmetic emulsion poses various problems: on account of the presence of water in the emulsion, flours will, on the one hand, grow bacteria, the growth of which is difficult to control and causes pollution of the emulsion. On the other hand, flours will swell by absorbing the water and give a starch which makes the emulsion unpleasant to apply. The fact that one or more flours are introduced into the lipid grains in the present invention makes it possible to protect the flour from the aqueous phase and thus to avoid the above-mentioned problems, while at the same time retaining the cleansing properties of the flours.

Preferred cereal flours which may be used in the composition of the present invention include soya flour, oat flour, wheat flour and *Triticum aestivum* wheat flour. Clays which may be used in the composition of the invention include kaolin. Make-up removing oils which may be used in the composition of the invention include 2-ethylhexyl palmitate, 2-diethylhexyl adipate, dioctyl adipate, diisopropyl adipate, 2-ethylhexyl hexanoate, ethyl laurate, methyl myristate, octyldodecyl octanoate, isodecyl neopentanoate, ethyl myristate, myristyl propionate, 2-ethylhexyl 2-ethylhexanoate, 2-ethylhexyl octanoate, 2-ethylhexyl caprate/caprylate, methyl palmitate, butyl myristate, isobutyl myristate, ethyl palmitate, isohexyl laurate, hexyl laurate and isopropyl isostearate.

The lipid grains according to the invention may also contain adjuvants chosen from hydrophilic or lipophilic active agents, fragrances, preserving agents, dyes, pigments, antioxidants, etc. The lipophilic or hydrophilic active agents are preferably hydrating active agents such an polyols, ceramides, and calmants such as green tea. It is advantageous to incorporate into the invention lipid grains heat-sensitive active agents such as vitamins; the reason for this is that these active agents cannot be introduced directly into the emulsion without being damaged since the emulsion is typically prepared under hot conditions and these active agents are readily degraded by heat, whereas their introduction into the lipid grains is performed at the melting temperature of the lipid substance or substances, that is to say at a temperature below 50° C.

The average diameter of the lipid grains may be within a very wide range, for example from 50 to 10,000 µm. It is, nevertheless, preferably within the range from 50 to 2000 µm and more particularly from 630 to 1200 µm.

According to a preferred embodiment of the invention, the lipid grains are obtained by very-low-temperature grinding. The preparation process consists in melting the lipid substance or substances on a water bath at a temperature 2°–3° C. above the melting zone of the lipid substances, in dispersing the adjuvants into the molten product, using an impeller, and then, after obtaining a homogeneous mixture, in removing the water bath and in allowing the mixture to cool to room temperature with stirring. Just before the mixture solidifies, the impeller is removed and the solid obtained is subjected to an abrupt freezing at a temperature below 0° C., and preferably between −80° C. and −120° C., using liquid nitrogen. Very-low-temperature grinding is then carried out until a particle size of between a few µm and a few mm is obtained. This process makes it possible to introduce the heat-sensitive active agents into the lipid grains without heating them, and thus without degrading them.

The lipid grains which may be used according to the invention may contain from 75% to 100% by weight, and preferably from 85% to 95% by weight, of lipid substances, from 0.5% to 10% by weight, and preferably from 1% to 5% by weight, of active agents, and from 0% to 5% by weight, preferably from 0.1% to 2% by weight, of other adjuvants. If they contain a compound for adjusting the hardness of the grains, in particular glyceryl monodiisostearate, these compounds may be present in an amount ranging from 0.01% to 20% by weight, and preferably from 0.01% to 15% by weight.

The composition according to the invention may contain from 0.5% to 10% by weight, and preferably from 0.5% to 5% by weight, of lipid grains relative to the total weight of the composition.

In the composition according to the invention, the oily phase may represent from 10% to 40% by weight relative to the total weight of the composition. Oils which may be used in the invention include vegetable oils including all plant oils obtained from leaves, seeds, etc., fruit oils, (e.g., those from the fruit meat, skins, almonds, etc. of fruit such as apricot oil), oils of animal origin, mineral oils (e.g., liquid petrolatum), synthetic oils, silicone-containing oils and/or fluoro oils. The oily phase may also contain other fatty substances such as fatty acids, fatty alcohols (e.g., cetyl alcohol) and waxes.

The composition according to the invention may further contain additives that are common in the cosmetics field, such as hydrophilic or lipophilic active agents, hydrophilic or lipophilic gelling agents, preserving agents, antioxidants, fragrances, fillers, screening agents, dyes, lipid vesicles, etc.

There may in particular be mentioned as active agents polyols such an glycerol, protein hydrolysates and ceramides. Depending on their nature, these adjuvants are used in the usual proportions for cosmetic compositions and, for example, from 0.01% to 10% by weight relative to the total weight of the composition, and, depending on their affinity, they are introduced into the aqueous phase or into the oily phase of the emulsion.

EXAMPLES

The examples which follow are given as a guide in order to gain a better understanding of the invention and are not limiting. The amounts indicated are percentages by weight.

EXAMPLE 1: Gentle cleansing product

| *Composition of the lipid grains: | |
|---|---|
| Lipocire DM (sold by the company Gattefosse) | 88% |
| Glyceryl monodiisostearate | 5% |
| Triticum aestivum wheat flour | 5% |
| Pigments | 2% |
| *Cosmetic composition: | |
| Oily phase: | |
| Cetearyl glucoside (Montanov 68 from the Seppic (emulsifying agent HLB = 10) | 4.25% |
| Cetyl alcohol | 0.75% |
| Apricot Oil | 25.00% |
| Aqueous phase: | |
| Xanthan gum (gelling agent) | 0.20% |
| Water | 64.80% |
| Lipid grains | 5% |

Preparation of the emulsion:

The cetearyl glucoside and the cetyl alcohol were heated to 80° C. and, in parallel, the apricot oil was heated to 60° C.; they were then mixed together homogeneously. Meanwhile, the aqueous phase was prepared by mixing together the xanthan gum and the water at 80° C. with stirring. The oily phase was then poured slowly into the aqueous phase with vigorous stirring. The mixture was left to cool to room temperature. The lipid grains obtained by very-low-temperature grinding (see above) are then added thereto.

The gentle cleansing product obtained has the appearance of a cream in which the colored lipid grains can be seen. These grains keep their color well over time and the emulsion remains white.

The product obtained was tested on a panel of 13 individuals with expertise in the cosmetics field, who applied it to the face every evening for one week. The product was judged to be highly innovative on account of its texture, very gentle to apply and very efficient for cleansing the skin. After application and rinsing, the skin of these individuals was soft, nourished and moisturized. Despite its effectiveness as an exfoliant, all of the individuals continued to use it daily without any problems.

COMPARATIVE EXAMPLE 1: Cleansing Product

| *Composition of the lipid grains: | |
|---|---|
| Lipocire DM (sold by Gattefosse) | 88% |
| Glyceryl monodiisostearate | 5% |
| Triticum aestivum wheat flour | 5% |
| Pigments | 2% |
| *Cosmetic composition: | |
| Oily phase: | |
| Sucrose stearate (sold under the name Crodesta F 160 by Corda) (emulsifying agent) | 3.00% |
| Sucrose stearate/sucrose distearate (mixture sold under the name Crodesta F 110 by Croda) (emulsifying agent) | 2.00% |
| Cetyl alcohol | 0.75% |
| Apricot oil | 25.00% |
| Aqueous phase: | |
| Xanthan gum (gelling agent) | 0.20% |
| Water | 64.05% |
| Lipid grains | 5% |

The preparation process was the same as in Example 1. The HLB value of the mixture of emulsifying agents used was 13.5.

In the product obtained, the emulsion takes the color of the grains on account of the diffusion of the pigments into the emulsion, and the grains become completely decolorized over time.

EXAMPLE 2: Gentle cleansing product

| *Composition of the lipid grains: | |
|---|---|
| Lipocire DM (sold by Gattefosse) | 88% |
| Glyceryl monodiisostearate | 5% |
| Oat flour | 5% |
| Pigments | 2% |
| *Cosmetic composition: | |
| Oily phase: | |
| Sorbitan tristearate (emulsifying agent) | 0.9% |
| PEG-40 stearate (emulsifying agent) | 2.0% |
| Cetyl alcohol | 2.5% |
| Apricot oil | 13.5% |
| Aqueous phase: | |
| Glycerol | 3.0% |
| Wheat protein hydrolysate | 0.5% |
| Water | 72.6% |
| Lipid grains | 5% |

The preparation process was the same as in Example 1. The HLB value of the mixture of emulsifying agents used was 12.3. A cream is obtained which cleanses well and leaves skin feeling soft.

COMPARATIVE EXAMPLE 2: Gentle cleansing Product

| *Composition of the lipid grains: | |
|---|---|
| Lipocire DM (sold by Gattefosse) | 88% |
| Glyceryl monodiisostearate | 5% |
| Oat flour | 5% |
| Pigments | 2% |

-continued

*Cosmetic composition:

Oily phase:

| | |
|---|---|
| Sucrose stearate (sold under the name Grilloten PSE 141G by Rita) (emulsifying agent) (HLB = 14.9) | 2.9% |
| Cetyl alcohol | 2.5% |
| Apricot oil | 13.5% |

Aqueous phase:

| | |
|---|---|
| Glycerol | 3.0% |
| Wheat protein hydrolysate | 0.5% |
| Water | 72.6% |
| Lipid grains | 5% |

The preparation process was the same as in Example 1. The HLB value of the emulsifying agent used was 14.9. During the study of the stability of the composition obtained at various temperatures, an increasingly intense coloration of the composition is observed, while the grains become increasingly bland and decolorized.

EXAMPLE 3: Make-up removing cream

*Composition of the lipid grains:

| | |
|---|---|
| Lipocire DM (sold by Gattefosse) | 88% |
| 2-ethylhexyl palmitate | 10% |
| Pigments | 2% |

*Cosmetic composition:

Oily phase:

| | |
|---|---|
| Glyceryl stearate (emulsifying agent) | 3% |
| PEG-50 stearate (emulsifying agent) | 3% |
| Cetyl alcohol | 5% |
| Liquid petrolatum | 12% |
| Volatile silicone oil | 12% |

Aqueous phase:

| | |
|---|---|
| Glycerol | 3% |
| Water qs | 95% |
| Lipid grains | 5% |

The preparation process was the same as in Example 1. The emulsifying agent used had an HLB value of 11. A make-up removing milk is obtained which cleanses the skin well while at the same time leaving it soft and moisturized.

EXAMPLE 4: Make-up removing milk

*Composition of the lipid grains:

| | |
|---|---|
| Lipocire DM (sold by Gattefosse) | 92% |
| Kaolin | 5% |
| Pigments | 3% |

*Cosmetic composition:

Oily phase:

| | |
|---|---|
| Glyceryl stearate/PEG-100 stearate (Arlacel 165 sold by ICI) (emulsifying agent) | 2.80 |
| Stearyl alcohol | 0.75 |
| Liquid lanolin | 0.30 |
| Liquid fraction of karite butter | 2.00 |
| Apricot almond oil | 14.0 |

Aqueous phase:

| | |
|---|---|
| Glycerol | 3.00 |
| Preserving agent | 0.10 |
| Water qs | 95% |
| Lipid grains | |

The preparation process was the same as in Example 1. The emulsifying agent used had an HLB value of 11. A make-up removing milk was obtained which cleanses the skin well while, at the same time, leaves it soft and moisturized.

EXAMPLE 5: Make-up removing milk

*Composition of the lipid grains:

| | |
|---|---|
| Lipocire DM (sold by Gattefosse) | 88% |
| Glyceryl monodiisostearate | 5% |
| *Triticum aestivum* wheat flour | 5% |
| Pigments | 2% |

*Cosmetic composition:

Oily phase:

| | |
|---|---|
| Sorbitan stearate (emulsifying agent) | 2.5 |
| Cetearyl octanoate | 11.0 |
| Volatile silicone oil | 5.0 |

Aqueous phase:

| | |
|---|---|
| Polysorbate 60 (emulsifying agent) | 2.5 |
| Carbomer | 0.5 |
| Glycerol | 5.0 |
| Water qs | 95% |
| Lipid grains | 5% |

The preparation process was the same as in Example 1. The mixture of emulsifying agents used had an HLB of 9.8. A make-up removing milk is obtained which cleanses the skin well while at the same time leaving it soft and moisturized.

This application is based on France 94-07481 filed Jun. 17, 1994, incorporated herein by reference.

What is claimed as new and is desired to be secured by Letters Patent of the United States is:

1. An oil-in-water emulsion comprising oil, water, an emulsifying agent having a hydrophilic-lipophilic balance below or equal to about 12.5 and present in an emulsifying amount, and solid non-hydrophilic lipid grains consisting essentially of at least one lipid and having a melting point below 50° C., said grains incorporating a cleansing agent, and wherein said grains have an average diameter ranging from 50 to 2000 μm in the emulsion without the grains fusing with the oil, and are present in an amount sufficient to provide skin cleansing, scrubbing, and caring action.

2. The emulsion according to claim 1, wherein the cleansing agent is selected from the group consisting of cereal flours, clays and make-up removing oils, and mixtures thereof.

3. The emulsion according to claim 1, wherein the emulsifying agent has a hydrophilic-lipophilic balance ranging from 6 to 12.

4. The emulsion according to claim 1, wherein the grains consist essentially of at least one solid, non-hydrophilic lipid substance selected from the group consisting of linear saturated fatty acid triglycerides having from 8 to 18 carbon atoms, butters or solid fractions of plant fatty substances and silicone waxes.

5. The emulsion according to claim 1, wherein, the grains are present in the emulsion in a proportion ranging from 0.5% to 10% by weight relative to the total weight of the emulsion.

6. The emulsion according to claim 1, wherein the grains are obtained by very-low-temperature grinding.

7. The emulsion according to claim 1, wherein the grains further comprise at least one adjuvant.

8. The emulsion according to claim 1, wherein the grains further comprise at least one heat-sensitive active agent.

9. The emulsion according to claim 1, wherein the oil represents from 10% to 40% by weight relative to the total weight of the emulsion.

10. The emulsion according to claim 1, wherein the emulsion further comprises at least one additive selected from the group consisting of gelling agents, hydrophilic or lipophilic active agents, fragrance, preserving agents, dyes and antioxidants.

11. The emulsion according to claim 1, wherein said emulsifying agent has a hydrophilic-lipophilic balance below or equal to 12.

12. A make-up removing composition comprising the emulsion of claim 1, wherein the cleansing agent has the ability to remove make-up.

13. A process for cleansing, scrubbing, or cleansing and scrubbing, skin, comprising applying to the skin the emulsion according to claim 1, massaging the skin with the emulsion in order to remove dead cells, and optionally rinsing the skin.

\* \* \* \* \*